United States Patent
Gupta et al.

(10) Patent No.: US 10,774,301 B2
(45) Date of Patent: Sep. 15, 2020

(54) SYRINGE SYSTEM FOR FLUID SEPARATION

(71) Applicant: Board of Trustees of Southern Illinois University, Springfield, IL (US)

(72) Inventors: Ashim Gupta, Springfield, IL (US); Michael W. Neumeister, Springfield, IL (US); Sohyung Cho, Clayton, MO (US)

(73) Assignee: Board of Trustees of Southern Illinois University, Springfield, IL (US)

( * ) Notice: Subject to any disclaimer, the term of this patent is extended or adjusted under 35 U.S.C. 154(b) by 410 days.

(21) Appl. No.: 15/645,657

(22) Filed: Jul. 10, 2017

(65) Prior Publication Data

US 2018/0010086 A1 Jan. 11, 2018

Related U.S. Application Data

(60) Provisional application No. 62/360,550, filed on Jul. 11, 2016.

(51) Int. Cl.
| | |
|---|---|
| *A61M 5/34* | (2006.01) |
| *A61M 5/315* | (2006.01) |
| *B01D 17/02* | (2006.01) |
| *C12M 1/00* | (2006.01) |

(52) U.S. Cl.
CPC ......... *C12M 47/04* (2013.01); *B01D 17/0214* (2013.01); *B01D 17/0217* (2013.01); *A61M 5/31511* (2013.01); *A61M 5/31566* (2013.01); *A61M 5/34* (2013.01)

(58) Field of Classification Search
CPC ......................... B01F 13/002; B01F 13/0023
See application file for complete search history.

(56) References Cited

U.S. PATENT DOCUMENTS

| | | | | |
|---|---|---|---|---|
| 1,799,463 | A * | 4/1931 | Hein | A61M 5/00 604/203 |
| 5,030,208 | A | 7/1991 | Novacek et al. | |
| 7,306,740 | B2 | 12/2007 | Freund | |
| 7,374,678 | B2 * | 5/2008 | Leach | B01L 3/502 210/380.1 |
| 8,926,487 | B2 | 1/2015 | Lee | |
| 8,968,272 | B2 | 3/2015 | Khouri | |
| 2009/0131878 | A1 * | 5/2009 | Kawamura | A61M 5/31511 604/228 |
| 2010/0249753 | A1 * | 9/2010 | Gaisser | A61B 17/8827 604/519 |
| 2011/0009830 | A1 * | 1/2011 | Kosinski | A61M 5/31511 604/227 |
| 2011/0166596 | A1 * | 7/2011 | Delmotte | A61J 1/2096 606/214 |
| 2011/0224612 | A1 * | 9/2011 | Lum | A61M 5/31511 604/125 |

\* cited by examiner

*Primary Examiner* — Marc C Howell
*Assistant Examiner* — Brittany I Fisher
(74) *Attorney, Agent, or Firm* — Robert Patino

(57) ABSTRACT

A syringe device for separating liquids of different densities is provided with a hollow syringe barrel, a perforated plunger seal with a seal hole, and a hollow plunging tube with a closed bottom with at least one tube hole. The perforated plunger seal has an outer perimeter that resides flush against an interior surface of the hollow syringe barrel. The tube hole is in operational relationship with the seal hole. Optionally, a relief hole is provided on a top portion of the hollow plunging tube to allow a user to create vacuum pressure as necessary.

8 Claims, 8 Drawing Sheets

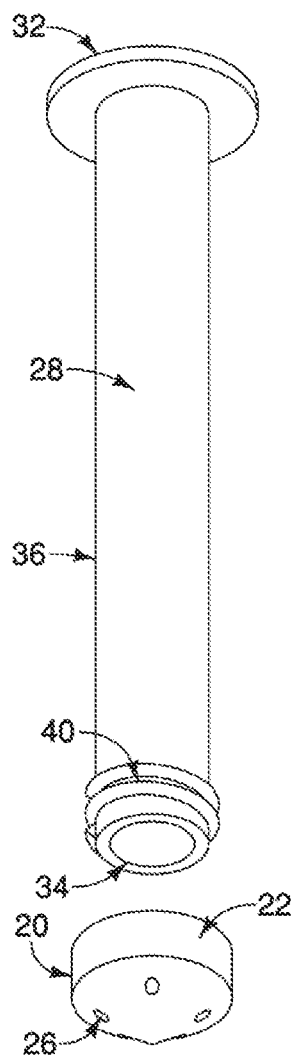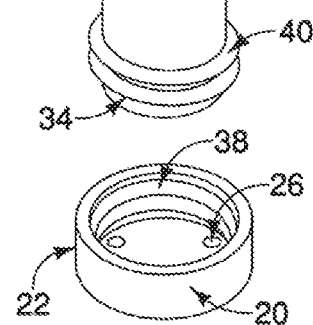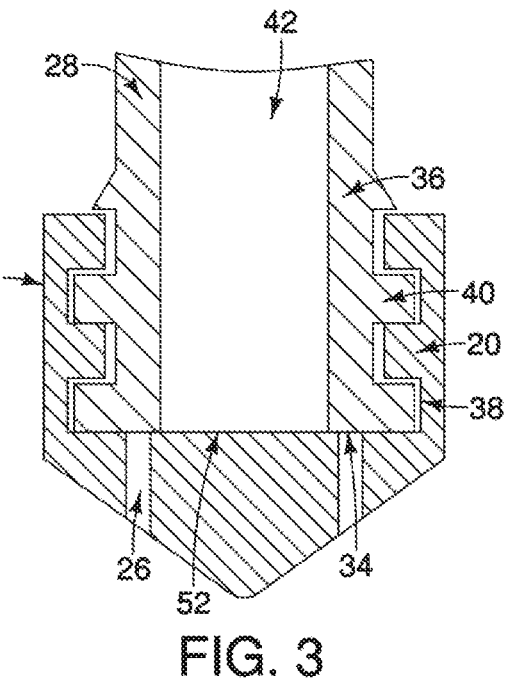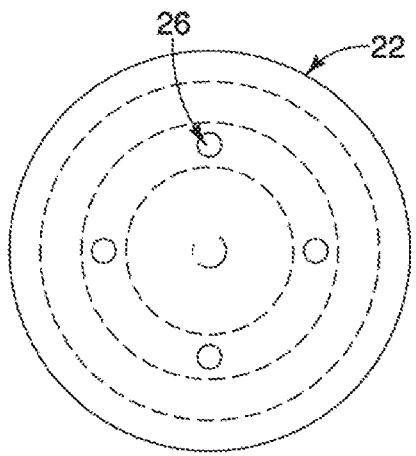
FIG. 1
FIG. 2
FIG. 3
FIG. 4

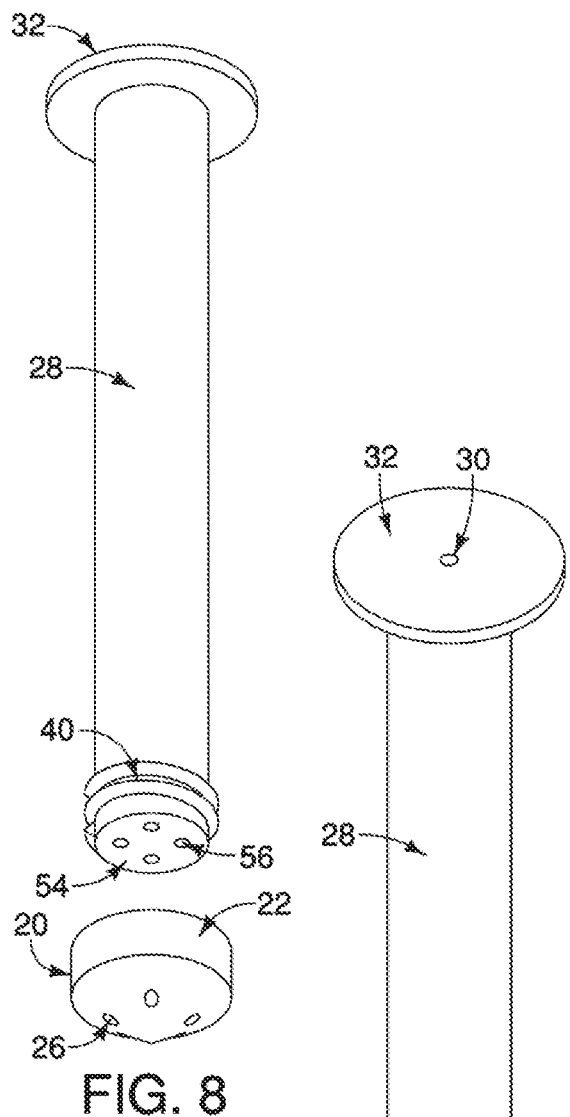
FIG. 8
FIG. 9
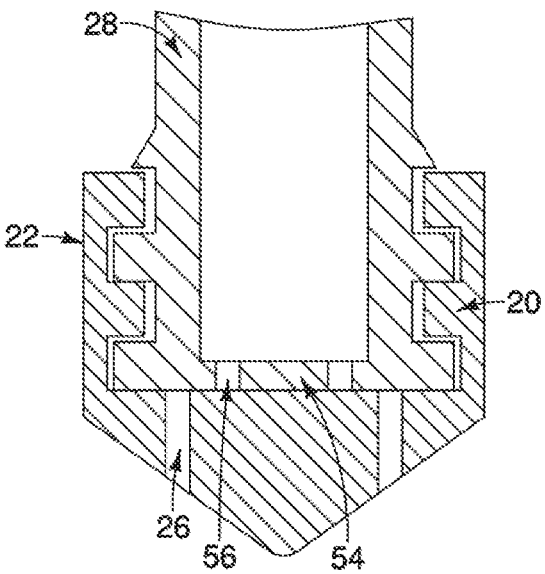
FIG. 10
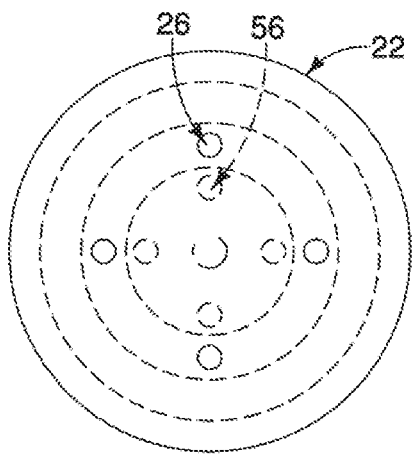
FIG. 11

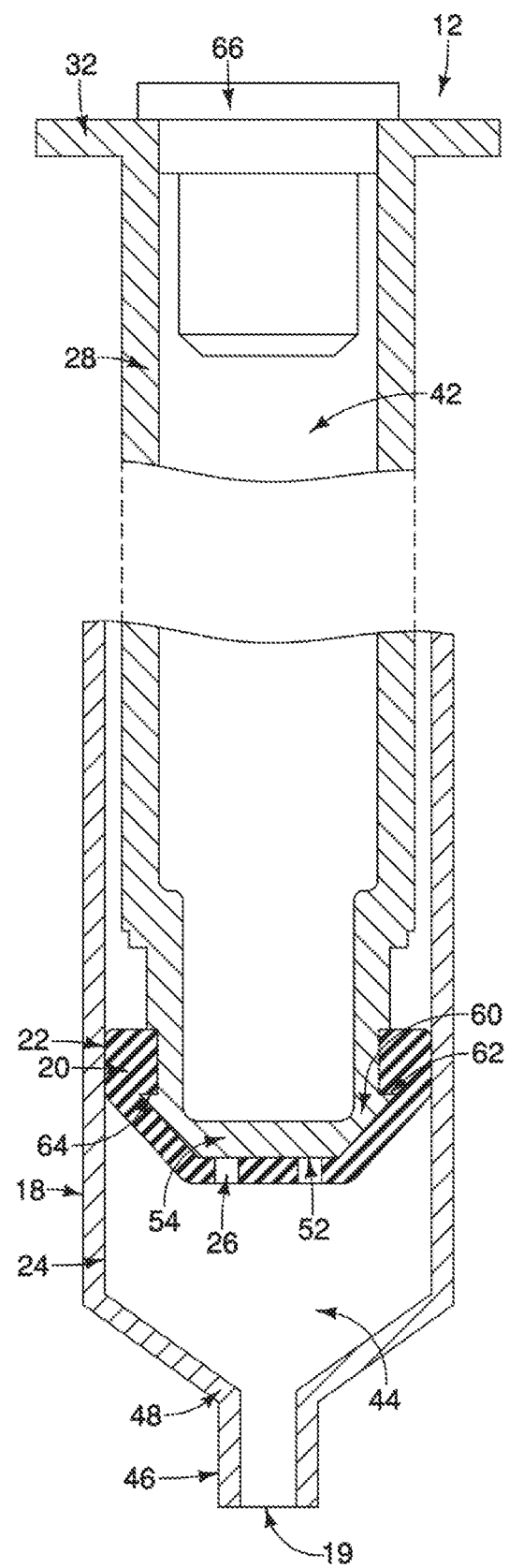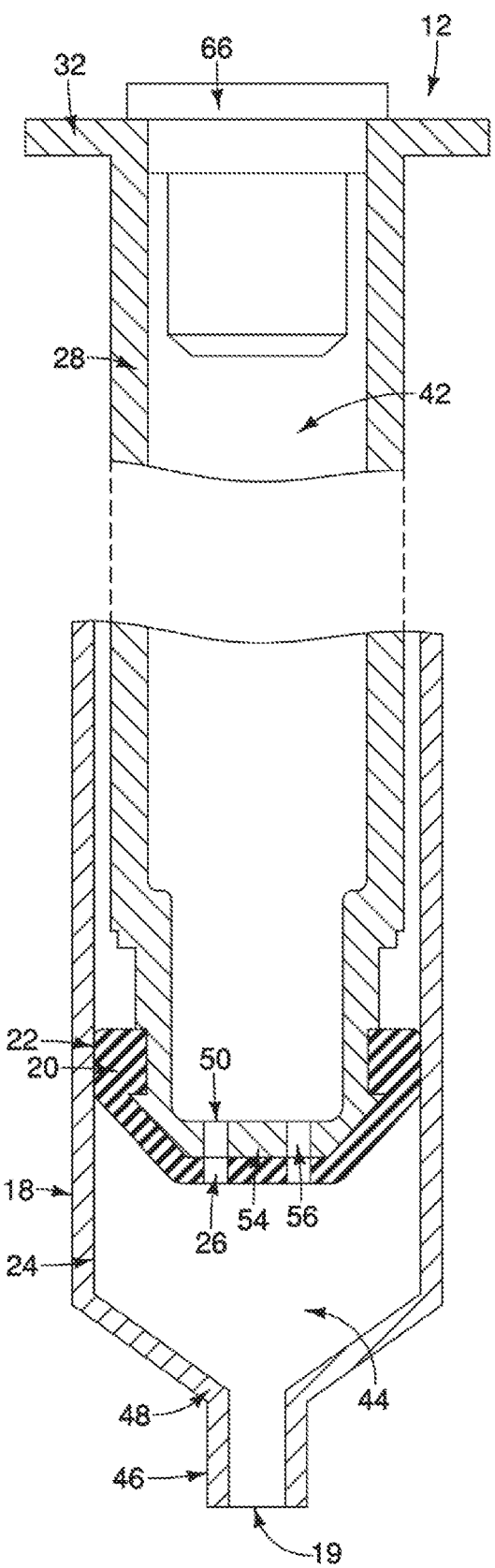
FIG. 16
FIG. 17

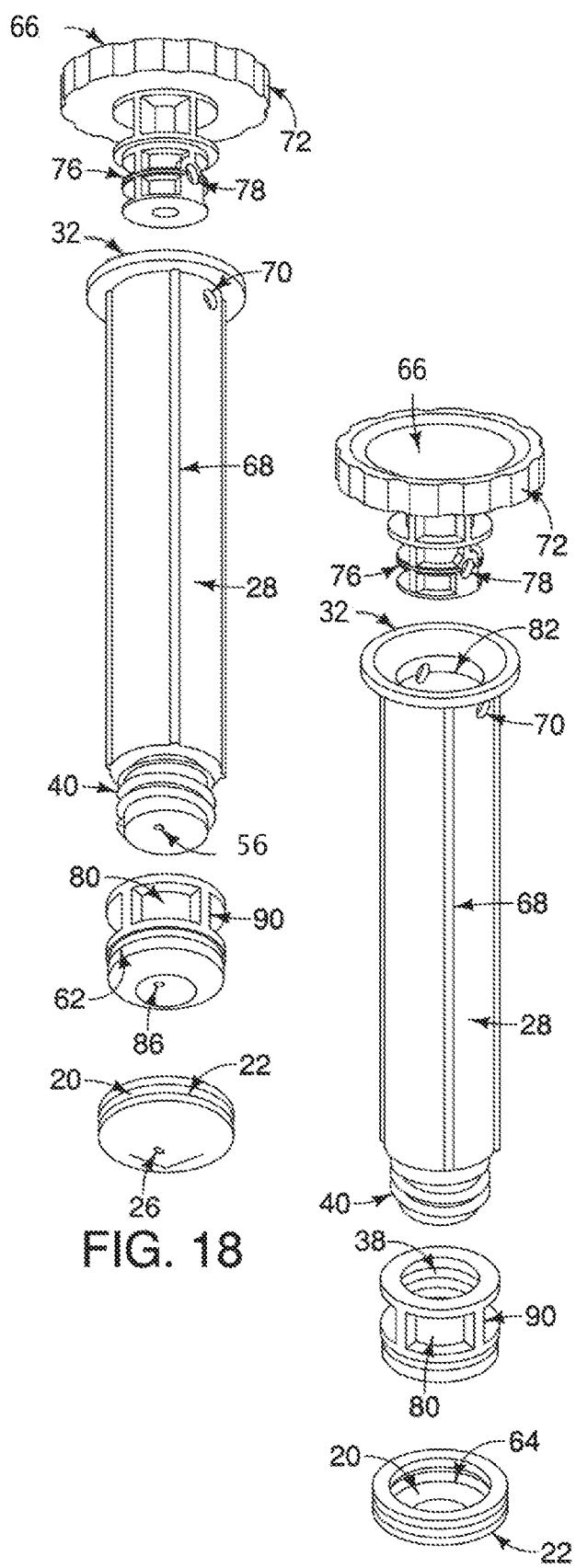
FIG. 18
FIG. 19
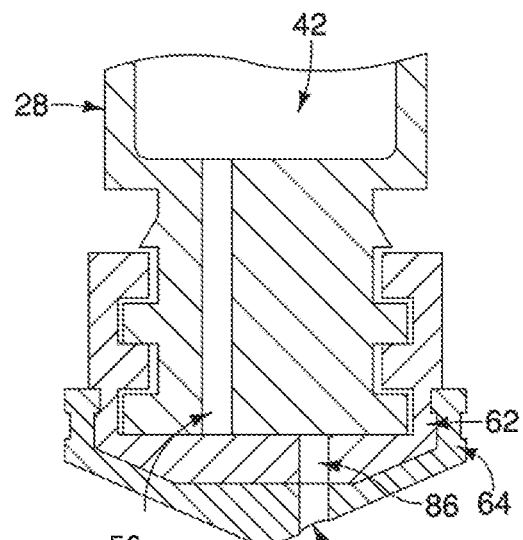
FIG. 20
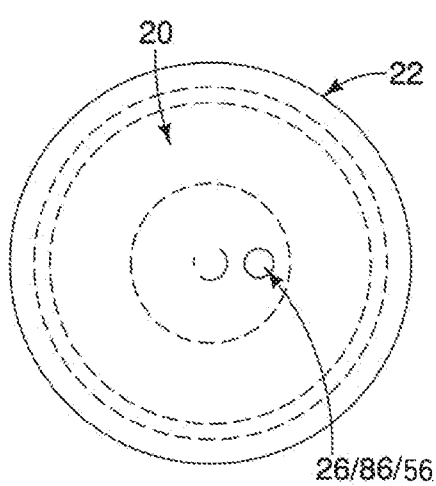
FIG. 21

SYRINGE SYSTEM FOR FLUID SEPARATION

BACKGROUND OF THE INVENTION

Autologous fat transfer, also known as fat grafting, has emerged as a widely used breast and facial reconstruction technique. Lipofilling, a form of fat grafting, has been used for several years, for example, to repair minor differences between a reconstructed breast and the non-reconstructed breast or to fill large dents in the body or face. Further uses include clinical applications to treat scleroderma, post-radiation skin damage, and skin rejuvenation. A surgeon performing a lipofilling procedure must go through several steps to obtain the fat cells necessary for grafting. After initial extraction by vacuum suction of raw lipoaspirate from the patient, the fat cells must be separated from the blood, debris, and oil in the lipoaspirate mixture.

One way to accomplish separation of fat cells is to allow gravity to separate out the layers naturally. This can be a slow, time-consuming process, taking approximately twenty to thirty minutes to achieve appropriate separation. Once separated, multiple syringes and other containers are employed to fully isolate the fat.

Another method to accomplish separation is by placing the suctioned fat in a cloth and squeezing the fat or allowing it to drain until the impurities are removed. This method is problematic because it is a complicated procedure, is time-consuming, and there is a greater risk of the fat cells becoming infected due to contact with the environment.

Still another method of separation is accomplished by placing the syringe in a centrifuge. The centrifuge rotates at approximately 1000 rpm for two to three minutes, allowing three layers to form: a more-dense blood and debris layer on the bottom, a desired fat cell layer in the middle, and a less-dense oil layer on top. Once separated, multiple syringes and containers must typically be employed to isolate the desired fat cells before the desired fat cells can be grafted back into the patient.

Methods of removing the oil layer from lipoaspirate solutions separated by gravity or centrifugation without the use of multiple containers and syringes remain inefficient and burdensome. The oil is trapped above the fat layer and cannot be discharged from conventional syringes or containers without prolonged effort. Each separation technique of the lipoaspirate that occurs in any of the above methods decreases the efficacy of the treatment as a whole for myriad reasons. Exposure of fat cells to potential contaminants or unnecessary trauma lead to an increase in potential infection or cell necrosis. Either of these conditions can cause serious complications in the patient or require further treatment to correct any issues. Potential risks to patient under sedation are also of concern. Typically, the longer a patient is under anesthesia, the greater the potential risk to a patient for an anesthesia-associated complication to occur.

As such, there is a need to reduce the required active steps involved in harvesting fat cells to increase the effectiveness, safety, and efficiency of the procedure. Fewer active steps would enhance the likelihood of the healthy fat cells being successfully grafted, reduce potential patient harm, and shorten the procedure to reduce the costs associated with the treatment.

BRIEF SUMMARY OF THE INVENTION

The abovementioned needs are solved by the present invention, which leverages a syringe system, preferably in combination with centrifugation, to enable fast liquid phase separation that allows the desired fat cells to be grafted into the body more quickly and with lower risk of contamination or fat cell damage. The present invention improves the separation and isolation of liquids with varying densities via a number of features. One such feature includes a means of separating liquids of different densities by allowing the less-dense liquids that form the top layer(s) of a separated solution to pass through a controllable opening in the device, effectively isolating the top layer(s) without having to use multiple syringes. Another feature includes the ability to keep separated liquids apart without exposing them to an outside environment. An additional feature includes a means of keeping the separated liquids from mixing as the desired liquids are returned to the host. As such, various embodiments are presented that improve the ability to separate fat cells from the oil layer in a separated lipoaspirate solution without having to use multiple containers and without further exposing the fat cells to the outside environment. It is also noted that this invention may be used in a similar manner for liquid solutions that contain varying densities (such as whole blood or hazardous waste) and is not intended to be limiting to lipoaspirate solutions.

In a first embodiment, a syringe device for separating liquids of different densities is provided with a hollow syringe barrel, a hollow plunging tube that is insertable into the hollow syringe barrel, and a perforated plunger seal that resides flush against an interior surface of the hollow syringe barrel when the plunging tube is inserted into the hollow syringe barrel. The perforated plunger seal has at least one seal hole that extends through the perforated plunger seal. A wall of the hollow plunging tube resides above the perforated plunging seal when the discharge opening is pointed down and is in operational relationship to the at least one seal hole. The term "above" here and throughout assumes a frame of reference where the end of the hollow syringe barrel that receives the hollow plunging tube is pointed upward and the end of the hollow plunging tube that connects to the perforated plunging seal is pointed downward. The hollow plunging tube is threadably coupled to the perforated plunger seal. When set to an open position, the seal hole allows liquids to flow from a hollow syringe barrel cavity into a hollow plunging tube cavity.

In a second embodiment, a syringe device for separating liquids of different densities is provided with a hollow syringe barrel, a hollow plunging tube with a sealed bottom, and a perforated plunger seal that resides flush against an interior surface of the hollow syringe barrel. The hollow plunging tube with a sealed bottom has at least one tube hole in the sealed bottom and the perforated plunger seal has at least one seal hole. The hollow plunging tube and perforated plunger seal are threadably connected by a male interlocking thread on the bottom portion of the hollow plunging tube and a female interlocking thread on the perforated plunger seal. A relief hole is optionally located on or near the top portion of the hollow plunging tube to provide for a vacuum as necessary.

In a third embodiment, a syringe device for separating liquids of different densities is provided with a hollow syringe barrel, a hollow plunging tube with a sealed bottom, and a perforated plunger seal that resides flush against an interior surface of the hollow syringe barrel. The perforated plunger seal has at least one seal hole. The hollow plunging tube with a sealed bottom is provided with at least one tube hole that passes through the sealed bottom. The at least one tube hole is in operational relationship with the at least one seal hole of the perforated plunger seal. The hollow plunging tube and the perforated plunger seal are flushly coupled by a lip on the hollow plunging tube with the sealed bottom.

In a fourth embodiment, a syringe device for separating liquids of different densities is provided with a hollow syringe barrel and a perforated plunger seal that resides flush against an interior surface of the hollow syringe barrel. The perforated plunger seal has at least one seal hole. A bottom portion adapter is further provided that has an at least one bottom portion adapter hole that corresponds with the at least one seal hole in said perforated plunger seal. Portions of the bottom portion adapter reside flush against the perforated plunger seal. A hollow plunging tube with a sealed bottom is also provided and resides in operational relationship with the bottom portion adapter. The hollow plunging tube has an at least one tube hole, a relief hole, and a top portion.

DESCRIPTION OF THE DRAWINGS

FIG. 1 illustrates a bottom-up, side perspective view of a hollow plunging tube and a corresponding perforated plunger seal in a first embodiment.

FIG. 2 illustrates a top-down, side perspective view of the hollow plunging tube and the corresponding perforated plunger seal in the first embodiment.

FIG. 3 illustrates a cross-sectional view of a bottom portion of the hollow plunging tube and the corresponding perforated plunger seal in a closed position in the first embodiment.

FIG. 4 illustrates a planar view from a bottom perspective of the perforated plunger seal and the hollow plunging tube in the first embodiment.

FIG. 8 illustrates a bottom-up, side perspective view of the hollow plunging tube and the corresponding perforated plunger seal in a second embodiment.

FIG. 9 illustrates a top-down, side perspective view of the hollow plunging tube and the corresponding perforated plunger seal in the second embodiment.

FIG. 10 illustrates a cross-sectional view of the bottom portion of the hollow plunging tube and the corresponding perforated plunger seal in the closed position in the second embodiment.

FIG. 11 illustrates a planar view from a bottom perspective of the perforated plunger seal and hollow plunging tube in the second embodiment.

FIG. 16 illustrates a cross-sectional view of a hollow syringe barrel, the hollow plunging tube, and the corresponding perforated plunger seal in the closed position for the third embodiment.

FIG. 17 illustrates a cross-sectional view of the hollow syringe barrel, the hollow plunging tube, and the corresponding perforated plunger seal in the open position for the third embodiment.

FIG. 18 illustrates a bottom-up, side perspective view of a removable stop cap, the hollow plunging tube, a bottom portion adapter, and the corresponding perforated plunger seal in a fourth embodiment.

FIG. 19 illustrates a top-down, side perspective of the removable stop cap, the hollow plunging tube, the bottom portion adapter, and the corresponding perforated plunger seal in the fourth embodiment.

FIG. 20 illustrates a cross-sectional view of a bottom portion of the hollow plunging tube, the bottom portion adapter, and the corresponding perforated plunger seal in the closed position in the fourth embodiment.

FIG. 21 illustrates a planar view from a bottom perspective of the hollow plunging tube, the bottom portion adapter, and the corresponding perforated plunger seal in the open position in the fourth embodiment.

DETAILED DESCRIPTION

Figure 7:
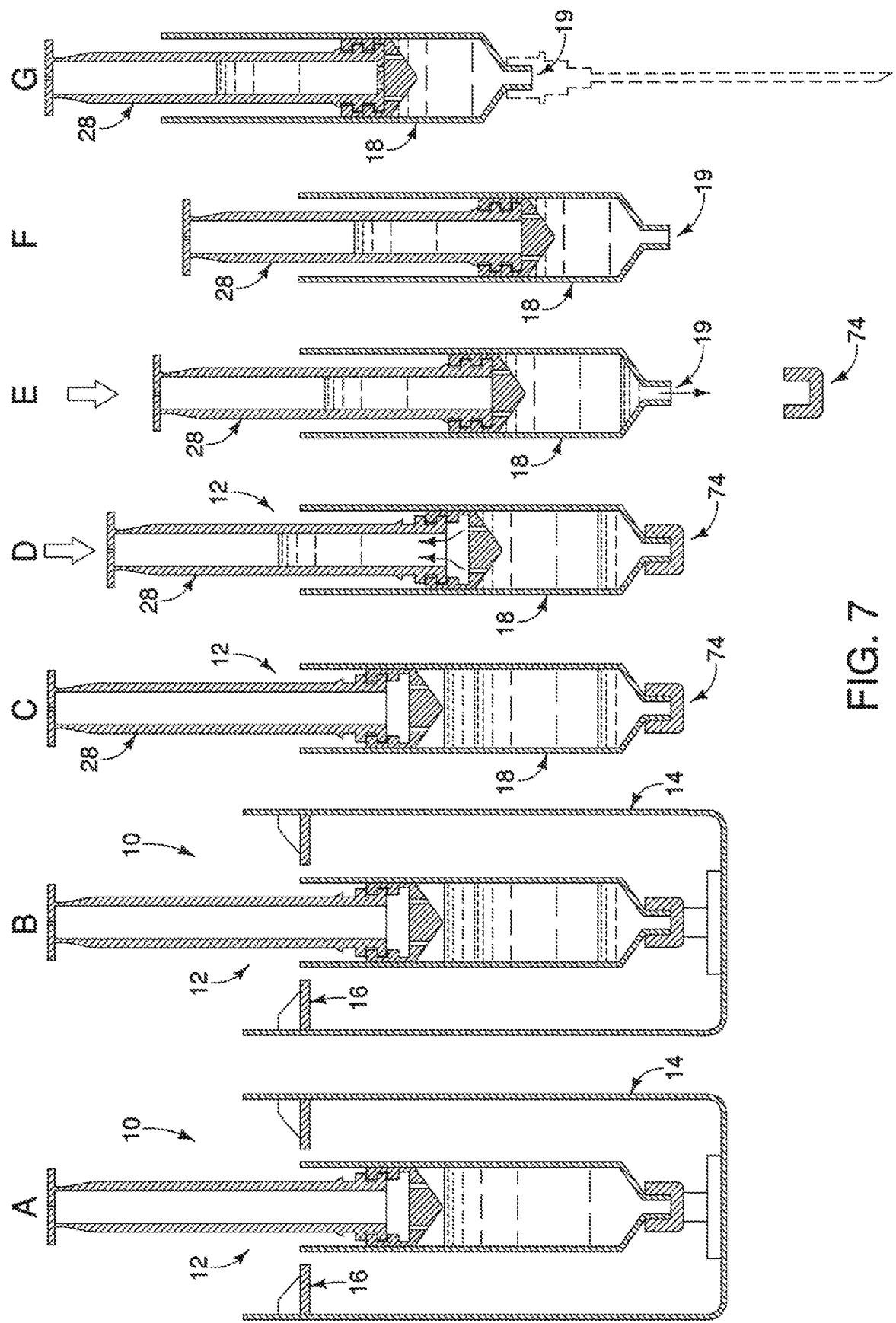
FIG. 7 illustrates the syringe system having an external tube with a support apparatus and a syringe device in the first embodiment in operation.
Figure 12:
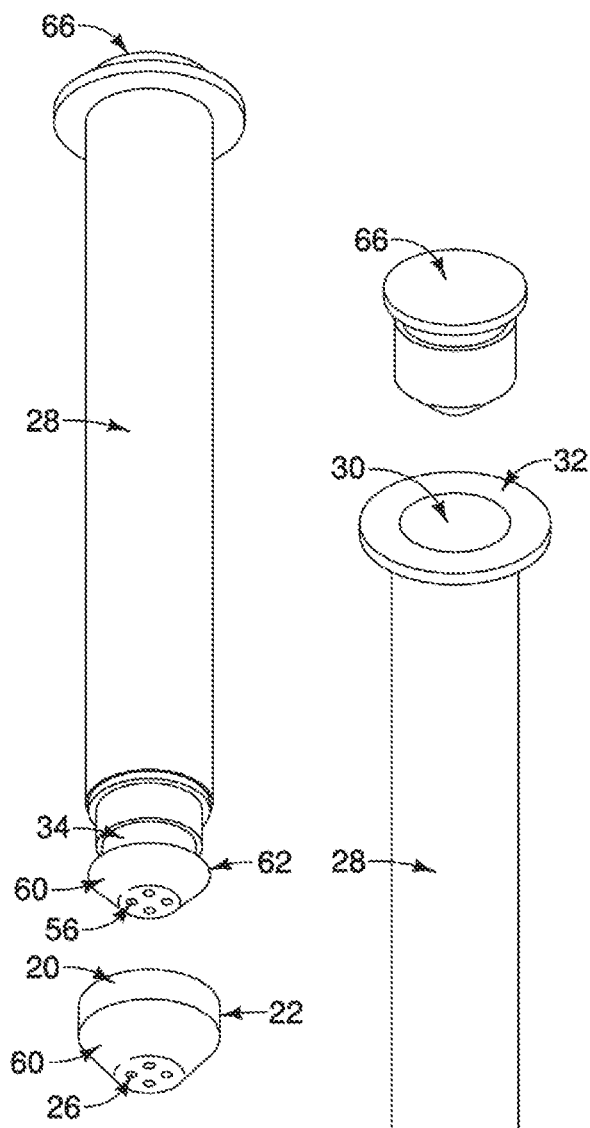
FIG. 12 illustrates a bottom-up, side perspective view of the hollow plunging tube and the corresponding perforated plunger seal for a third embodiment.
Figure 13:
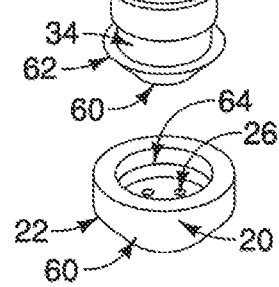
FIG. 13 illustrates a top-down, side perspective view of the hollow plunging tube, removable stop cap, and corresponding perforated plunger seal for the third embodiment.

A syringe system 10 for separating fluids of varying densities is provided with a syringe device 12 and an optional external tube 14 as illustrated in FIG. 7. The external tube 14 is used as a holding chamber to support the syringe device 12, for instance as it goes through a spin cycle within a centrifuge (not shown). A support apparatus 16 may be used to help keep the syringe device 12 secure while the syringe device 12 is being subjected to the spin cycle. Once the liquids are separated within the syringe device 12, a process can begin to extract the separated liquid layers away from each other for use.

In one application, there is a need to isolate fat cells when fat grafting in an expedited manner. In this instance, the liquids of varying densities may be defined as oil, fat cells, and blood/debris components resulting from fat collection. When liposuction or other fat collection processes are used to remove fat from the body, a mixture is collected as shown in the first illustration of FIG. 7 and undesirable oil and debris need to be separated and removed from the fat cells. The quickest means of separating these liquids is to centrifuge the collected mixture, which creates a top oil layer (or light density liquid), a middle layer of fat cells (or middle density liquid), and a bottom blood/debris layer (or heavy density liquid) as shown in the second illustration of FIG. 7. The desired middle fat cell layer is difficult to isolate in an expedited manner. The embodiments as discussed herein illustrate varying mechanisms in which the top oil layer (or light density liquid) can be extracted from a hollow syringe barrel 18 and the bottom debris layer (or heavy density liquid) may be discharged through a discharge opening 19.

The syringe system 10 can also be used to separate multiple layers within an extracted mixture. For the exemplary application, three liquid densities are used to differentiate the separation of the collected mixture by the syringe device 12, but the syringe system may alternatively be applied to separate more than three layers. The syringe device 12 may also be operated with inverted directionality such that the light density liquid layer(s) settle adjacent to the discharge opening 19. For the purposes of maintaining continuity within the liposuction example, the syringe device as described throughout is assumed to be oriented such that the discharge opening 19 is pointed downward and the three liquid layers as described above (the top oil layer, the middle layer of fat cells, and the bottom blood/debris layer) are referred to from here and throughout as light density layer (the liquid closest to the hollow plunging tube 28), middle density layer (the liquid that does not touch the hollow plunging tube 28 nor the lower end 48 of the hollow syringe barrel 18), and heavy density layer (the liquid closest to the lower end 48 of the hollow syringe barrel 18).

Now referring to FIGS. 1-6, a first embodiment is shown and is provided with the hollow syringe barrel 18 to contain the unseparated solution or separated layer(s), as applicable given the stage of processing and isolation of the material. The hollow syringe barrel 18 is preferably made of a hard durable material such as a rigid plastic, ceramic, or metal. Also provided is a perforated plunger seal 20 with an outer perimeter 22 that resides flush against an interior surface 24 of the hollow syringe barrel 18 and is provided with an at least one seal hole 26. The perforated plunger seal 20 is preferably made of a softer, more pliable material, such as a rubber or soft plastic, to create an effective seal against the interior surface 24 of the hollow syringe barrel 18. In a preferred embodiment, 2 to 4 seal holes are used, but 1 to more than 4 seal holes may be used.

A hollow plunging tube 28 is provided that is threadably coupled to the perforated plunger seal 20. The hollow plunging tube 28 is optionally provided with an at least one relief hole 30 located on a top portion 32 of the hollow plunging tube 28. Alternatively, the at least one relief hole 30 may be located in an upper portion of the hollow plunging tube 28 as illustrated in FIG. 19, where the upper portion includes the top quarter of the hollow plunging tube 28 and includes both a wall 36 of the hollow plunging tube 28 and the top portion 32. The relief hole 30 is used to allow air to escape from the hollow plunging tube 28 as the hollow plunging tube 28 absorbs the light density liquid (fourth illustration from left in FIG. 7). A bottom portion 34 of the wall 36 of the hollow plunging tube 28 resides above and is in operational relationship to the at least one seal hole 26. An at least one female interlocking thread 38 on the perforated plunger seal 20 is aligned to correspond with an at least one male interlocking thread 40 located adjacent to the bottom portion 34 of the hollow plunging tube 28. The at least one seal hole 26 in the perforated plunger seal 20 communicates a hollow plunging tube cavity 42 within the hollow plunging tube 28 with a hollow syringe barrel cavity 44 located within the hollow syringe barrel 18 when the hollow plunging tube 28 is in an open position 50.

A beveled needle hub 46 on a lower end 48 of the hollow syringe barrel 18 allows liquids to be pushed out of the hollow syringe barrel cavity 44. During operation, a solution or material is introduced to the hollow syringe barrel cavity and the liquids of varying densities separate either through settling (e.g. gravity-assisted) or centrifugal force. The heavy density liquid settles at the bottom and can be expelled through the discharge opening 19. Once all of the heavy density liquid is removed, the middle density liquid (or in the described application, this will be the healthy fat cells) will settle within the syringe barrel cavity 44 in the lower end 48 to become the next liquid ready to be discharged from the hollow syringe barrel cavity 44.

Figure 5:
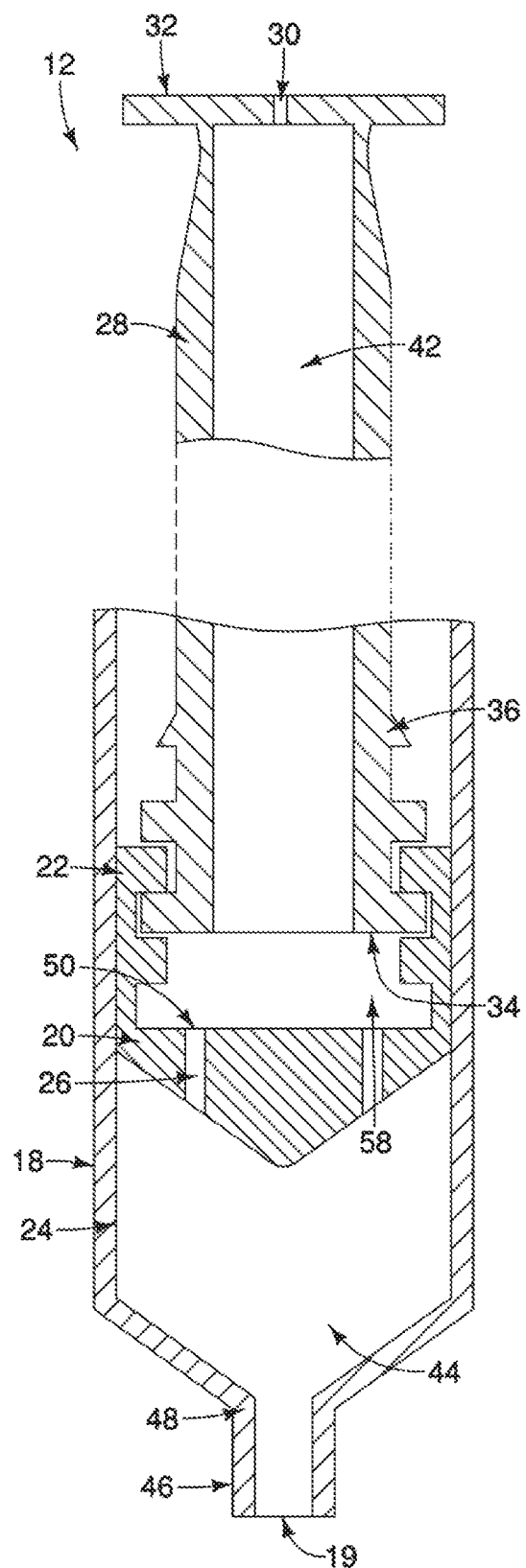
FIG. 5 illustrates a cross-sectional view of a hollow syringe barrel, the hollow plunging tube, and the corresponding perforated plunger seal set to an open position in the first embodiment.

Now referring to FIG. 5, the hollow plunging tube 28 is situated in the open position 50. This open position 50 is set prior to operation by rotating the hollow plunging tube 28 within the hollow syringe barrel 18 with respect to the perforated plunger seal 20 to set the hollow plunging tube 28 to the open position 50. In some embodiments, this rotation may be realized when the hollow plunging tube 28 and attached perforated plunger seal 20 are inserted in the hollow syringe barrel 18 by rotating the hollow plunging tube 28 with respect to the hollow syringe barrel 18, where friction between the hollow syringe barrel 18 and the perforated plunger seal 20 results in differential rotations (and thus, rotation with respect to one another) of the hollow plunging tube 28 and the perforated plunger seal 20. The at least one seal hole 26 permits liquids to flow between the hollow syringe barrel cavity 44 and the hollow plunging tube cavity 42 when the hollow plunging tube 28 is in the open position 50.

Figure 6:
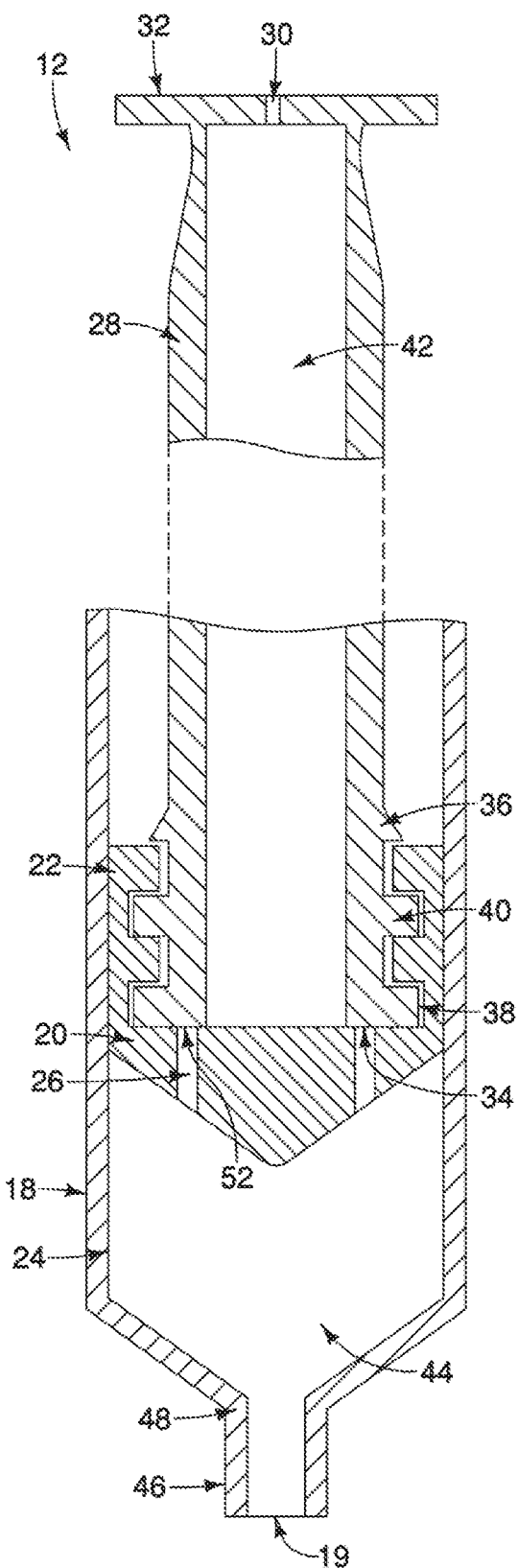
FIG. 6 illustrates a cross-sectional view of the hollow syringe barrel, the hollow plunging tube, and the corresponding perforated plunger seal set to a closed position in the first embodiment.

Now referring to FIGS. 3 and 6, the hollow plunging tube 28 is rotated to set the hollow plunging tube 28 to a closed position 52. In the closed position 52, the at least one seal hole 26 is covered by the bottom portion 34 of the hollow plunging tube 28, thus preventing the flow of liquids between the hollow syringe barrel cavity 44 and the hollow plunging tube cavity 42.

Now referring to FIGS. 8-11, a second embodiment is illustrated. The second embodiment is provided with a hollow syringe barrel 18 (analogous to that shown in FIGS. 5-6) to contain the unseparated solution or separated layer(s), as applicable given the stage of processing and isolation of the liquid. As in the first embodiment, a perforated plunger seal 20 which has an outer perimeter 22 that resides flush against an interior surface 24 of the hollow syringe barrel 18 is provided with an at least one seal hole 26. In a preferred embodiment, 2 to 4 seal holes are used, but 1 to more than 4 seal holes may be used. A hollow plunging tube 28 is provided with a sealed bottom 54. The hollow plunging tube 28 is threadably coupled to the perforated plunger seal 20 via an at least one male interlocking thread 40 adjacent to the sealed bottom 54. The at least one female interlocking thread 38 on the perforated plunger seal 20 is aligned to correspond with at least one male interlocking thread 40 located on the bottom portion 34 of the hollow plunging tube 28. The hollow plunging tube 28 is optionally provided with at least one relief hole 30 located in an upper portion of the hollow plunging tube 28 as illustrated in FIG. 19, where the upper portion includes the top quarter of the hollow plunging tube 28 and includes both a wall 36 of the hollow plunging tube 28 and the top portion 32. The sealed bottom 54 of the hollow plunging tube 28 is provided with an at least one tube hole 56. In a preferred embodiment, 2 to 4 tube holes are used but 1 to more than 4 tube holes may be used. In operation, a beveled needle hub 46 on the lower end 48 of the hollow syringe barrel 18 allows liquids to be pushed out of the hollow syringe barrel cavity 44.

The second embodiment allows for the hollow plunging tube 28 to be rotated with respect to the perforated plunger seal 20 to set said hollow plunging tube 28 to the open position 50; this operation is analogous to that shown in FIG.

5 for the first embodiment. The hollow plunging tube 28 set to the open position 50 creates a seal cavity 58 within the perforated plunger seal 20. In the open position, the at least one seal hole 26 permits liquids to flow from the hollow syringe barrel cavity 44, through the seal cavity 58, through the one or more tube holes 56, and into the hollow plunging tube cavity 42.

Now referring to FIG. 10, the hollow plunging tube 28 is rotated with respect to the perforated plunger seal 20 to set the hollow plunging tube 28 to the closed position. The seal cavity 58 is thus collapsed while the at least one seal hole 26 and the at least one tube hole 56 are misaligned, preventing the flow of liquids between the hollow syringe barrel cavity 44 and the hollow plunging tube cavity 42.

Now referring to FIGS. 12-17, a third embodiment is illustrated. The third embodiment is provided with a hollow syringe barrel 18 to contain the liquid. As in the previous embodiments, a perforated plunger seal 20 is provided that has an outer perimeter 22 which resides flush against an interior surface 24 of the hollow syringe barrel 18 and is provided with an at least one seal hole 26. In a preferred embodiment, 2 to 4 seal holes are used, but 1 to more than 4 seal holes may be used. A hollow plunging tube 28 is provided with a sealed bottom 54 with an at least one tube hole 56. The at least one tube hole 56 resides in operational relationship to the at least one seal hole 26. In a preferred embodiment, 2 to 4 tube holes are used but 1 to more than 4 tube holes may be used. It is preferred that the bottom portion 34 of the hollow plunging tube 28 is a conical trapezoidal shape 60 that fits flushly within the perforated plunger seal 20 when in an open or a closed position; however, it is understood that other shapes may be used, for instance, to accommodate alternative shapes of a perforated plunger seal 20.

The hollow plunging tube 28 is coupled flushly by a lip 62 on the conical trapezodial shape 60 of the hollow plunging tube 28 when inserted into an interior groove 64 of the trapezoidal shape perforated plunger seal 20. A beveled needle hub 46 on the lower end 48 of the hollow syringe barrel 18 allows liquids to be pushed out of the hollow syringe barrel cavity 44. An optional relief hole 30 is located on the top portion 32 of the hollow plunging tube 28. Alternatively, the at least one relief hole 30 may be located on the side of the hollow plunging tube 28; in such embodiments, the at least one relief hole 30 will preferably be located within the upper half of the hollow plunging tube 28 and more preferably will be located within the upper quarter of the hollow plunging tube 28. An optional feature of this embodiment is a removable stop cap 66 that is used to seal the relief hole 30 and enable creation of a vacuum within the hollow plunging tube 28.

Figure 14:
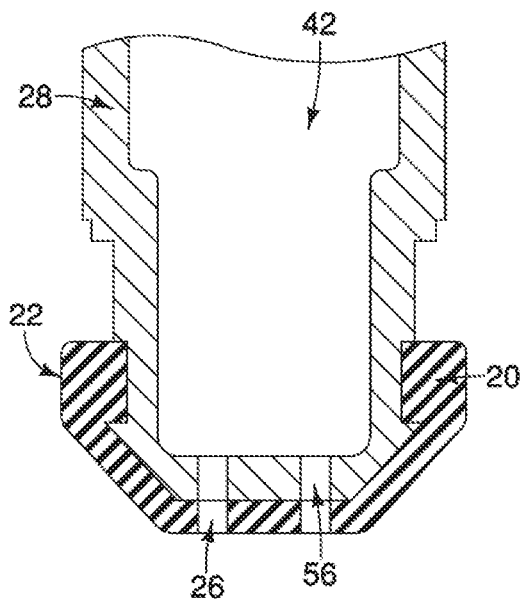
FIG. 14 illustrates a cross-sectional view of the bottom portion of the hollow plunging tube and the corresponding perforated plunger seal in the open position for the third embodiment.
Figure 15:
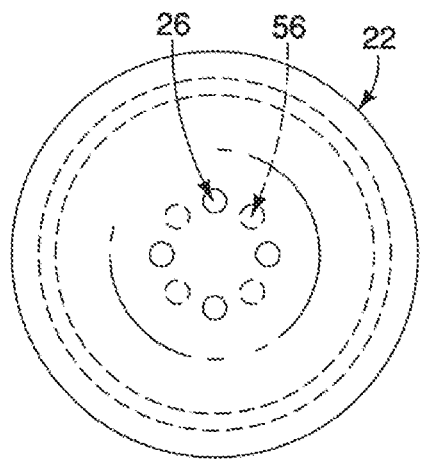
FIG. 15 illustrates a planar view from a bottom perspective of the perforated plunger seal and the hollow plunging tube for the third embodiment.
Figure 22:
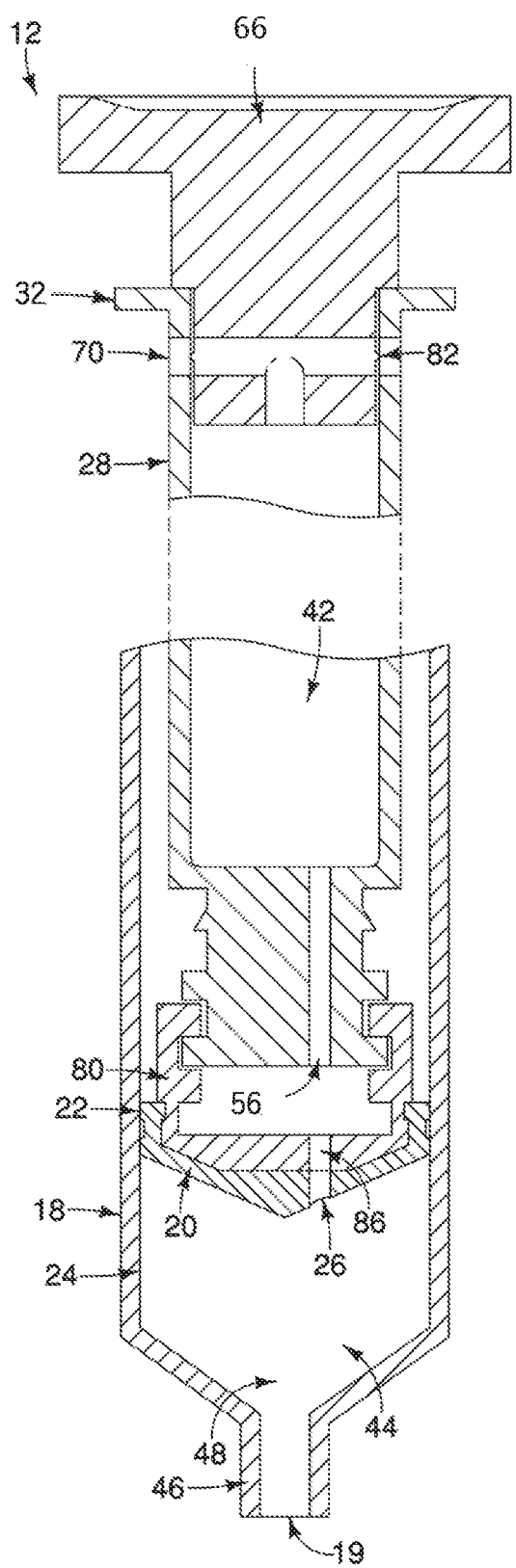
FIG. 22 illustrates a cross-sectional view of the removable stop cap, the hollow plunging tube, the bottom portion adapter, the corresponding perforated plunger seal, and the hollow syringe barrel set to the open position in the fourth embodiment.

Now referring to FIGS. 14 and 17, the hollow plunging tube 28 is rotated to the open position 50 so that at least one tube hole 56 and the at least one seal hole 26 align. The open position 50 allows the adjacent liquids to pass between the hollow syringe barrel cavity 44 and the hollow plunging tube cavity 42.

Now referring to FIG. 16, the hollow plunging tube 28 is rotated to a closed position 52 so that at least one tube hole 56 and the corresponding at least one seal hole 26 are misaligned. The closed position 52 prevents adjacent liquids from passing between the hollow syringe barrel cavity 44 and the hollow plunging tube cavity 42.

Now referring to FIGS. 18-23, a fourth embodiment is illustrated. The fourth embodiment is provided with a hollow syringe barrel 18 to contain the liquid. As in the previous embodiments, a perforated plunger seal 20 is provided that has an outer perimeter 22, which resides flush against an interior surface 24 of the hollow syringe barrel 18 and is provided with an at least one seal hole 26. In a preferred embodiment, 2 to 4 seal holes are used, but 1 to more than 4 seal holes may be used. The bottom portion adapter 80 resides in operational proximity to said perforated plunger seal 20. The perforated plunger seal 20 is attached to a bottom portion adapter 80 such that the seal hole 26 aligns with the bottom portion adapter hole 86. As in the third embodiment, a lip 62 is optionally provided and is located on the bottom portion adapter 80; this lip 62 corresponds to an interior grove 64 located on the interior of the perforated plunger seal 20. In the preferred embodiment, the bottom portion adapter 80 resides flush against the perforated plunger seal 20 to create a continuous piece; however, it is noted that the bottom portion adapter 80 may optionally reside partially flush against the perforated plunger seal 20 to achieve a similar effect of a continuous piece. The bottom portion adapter 80 threadably corresponds to the hollow plunging tube 28 which features a sealed bottom 54 perforated by an at least one tube hole 56.

Figure 23:
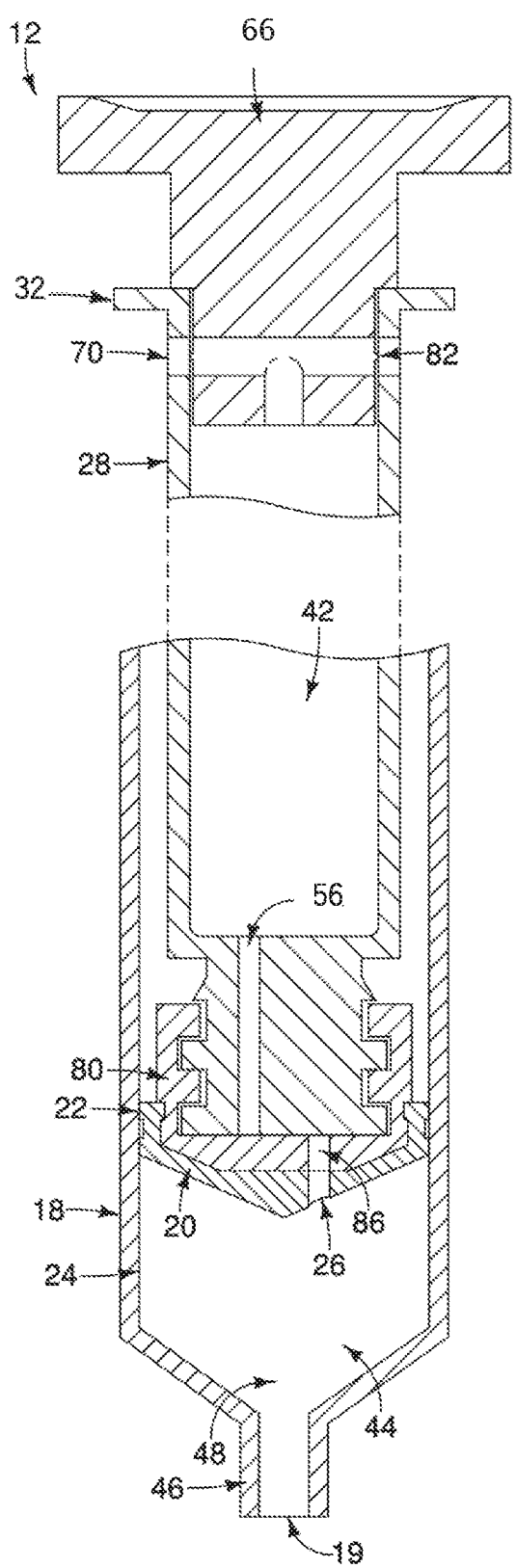
FIG. 23 illustrates a cross-sectional view of the removable stop cap, the hollow plunging tube, the bottom portion adapter, the corresponding perforated plunger seal, and the hollow syringe barrel set to the closed position in the fourth embodiment.

The bottom portion adapter hole 86 is positioned below the tube hole 56 by rotating the hollow plunging tube 28 to the open position. This rotation is realized by rotating the hollow plunging tube 28 with respect to the syringe tube, where friction between the perforated plunger seal 20 and the interior surface 24 hold the perforated plunger seal 20 and the bottom adapter portion 80 stationary with respect to the hollow syringe barrel 18. In the open position of this embodiment, sufficient space is created to form a passage cavity that allows fluids to flow from the hollow syringe barrel cavity 44 to the hollow plunging tube cavity 42. When the hollow plunging tube 28 is rotated in a direction to advance the sealed bottom 54 into the bottom portion adaptor 80, the sealed bottom 54 will stop advancing when the sealed bottom 54 resides flush with a lower end of the bottom portion adaptor 80. This position is referred to as the closed position where liquids are prevented from flowing between the hollow syringe barrel cavity 44 of the hollow syringe barrel 18 and the hollow plunging tube cavity 42 of the hollow plunging tube 28. At this closed position, the bottom portion adapter hole 86 is not aligned with the tube hole 56. This closed position is illustrated in FIG. 20 and FIG. 23.

In a preferred embodiment, a removable stop cap 66 is insertable into the top portion 32; the removable stop cap 66 is optionally provided with a ridged edging 72. The ridged edging 72 comprises of indentations to accommodate simple gripping, but the ridged edging may also comprise of other known gripping edging as are well known in the art. Also, the hollow plunging tube 28 may optionally be provided with ridges 68 as well. In a preferred embodiment, the hollow plunging tube 28 is provided with an at least one ridge 68. Most preferably, 2-4 ridges 68 are provided, but there may be more than 4, which increases the stability of the hollow plunging tube 28 within the hollow syringe barrel 18. The bottom portion adapter 80 has an option for bottom portion adapter ridges 90. The purpose for the ridged edging 72, the additional ridges 68, and the bottom portion adapter ridges 90 is to maintain stability, create a firm grip between the user and the device itself, and to reduce the amount of material necessary to create each element.

The removable stop cap 66 is insertable into the hollow plunging tube 28. The removable stop cap has a side relief hole ridge 76 that coincides with a hollow plunging tube notch 82 located in the hollow plunging tube 28. The side relief hole ridge 76 stabilizes the removable stop cap 66 when placed inside the hollow plunging tube 28. Then the removable stop cap rotates to a relief position wherein the at least one top portion relief hole 78 aligns with an at least one side relief hole 70 located on the hollow plunging tube 28, thereby creating a means to allow fluids to escape from within a hollow plunging tube cavity 42 of said hollow plunging tube 28. Conversely, the removable stop cap 66 is rotatable to a sealed position wherein the at least one top portion relief hole on the top portion misaligns with the at least one side relief hole located on the hollow plunging tube creating a seal within the hollow plunging tube cavity of the hollow plunging tube to prevent fluids from escaping. Alternatively to the specific side relief hole described above, the fourth embodiment may include at least one relief hole 30 located in an upper portion of the hollow plunging tube 28 as illustrated in FIG. 19, where the upper portion includes the top quarter of the hollow plunging tube 28 and includes both a wall 36 of the hollow plunging tube 28 and the removable stop cap 66.

Now referring to illustrations C and D in FIG. 7, operations of the above described embodiments are substantially similar. After the liquids have been separated, the light density liquid is extracted into the hollow plunging tube 28 as force is exerted in a downward motion on the hollow plunging tube 28 resulting in a position change of the hollow plunging tube 28 within the hollow syringe barrel 18. Once the hollow plunging tube 28 has captured substantially all of the light density liquid, the hollow plunging tube is moved from an open position 50 to a closed position 52. In the presently described embodiments, the movement from an open position 50 to a closed position 52 is created by rotating the hollow plunging tube 28 in relation to the male interlocking thread 40. A hub cap 74 can then be removed to allow the heavy density liquid to be removed from the discharge opening 19 as shown in illustrations E and F in FIG. 7. Once the hub cap 74 is removed, the hollow plunging tube 28 may be advanced further in a downward direction into the hollow syringe barrel 18 until substantially all or all of the heavy density liquid is removed. Once this operation is complete, the hub cap 74 may be reinserted to preserve the middle density liquid, in the case of the exemplary application discussed herein, until ready for use. When the syringe device 12 is ready for operation, a needle or other delivery piece may be employed on the beveled needle hub 46 to deploy the middle density liquid.

While several particular embodiments of the present invention have been described herein, it will be appreciated by those skilled in the art that changes and modifications may be made thereto without departing from the invention in its broader aspects and as set forth in the following claims.

We claim:

1. A syringe device for separating liquids of different densities comprising of:
   a hollow syringe barrel,
   a perforated plunger seal with an outer perimeter that resides flush against an interior surface of said hollow syringe barrel with an at least one seal hole in said perforated plunger seal,
   a hollow plunging tube with a scaled bottom with an at least one tube hole in said scaled bottom of scaled hollow plunging tube,
   a removable stop cap in operational relationship with said hollow plunging tube, and
   said removable stop cap is rotatable to a scaled position wherein an at least one top portion relief hole on said removable stop cap misaligns with an at least one side relief hole located on said hollow plunging tube creating a seal within a hollow plunging tube cavity of said hollow plunging tube to prevent fluids from escaping.

2. The syringe device of claim 1 further comprising:
   a beveled needle hub at a lower end of said hollow syringe barrel.

3. The syringe device of claim 1 wherein:
   said at least one tube hole on said sealed bottom of said hollow plunging tube is in operational relationship to an at least one seal hole in said perforated plunger seal.

4. The syringe device of claim 3 wherein:
   An at least one male interlocking thread located at a bottom portion of said hollow plunging tube resides in operational relationship with a female interlocking thread of said perforated plunger seal.

5. The syringe device of claim 4 wherein:
   Said at least one tube hole on said sealed bottom of said hollow plunging tube is aligned to correspond with said at least one seal hole in said perforated plunger seal.

6. The syringe device of claim 5 wherein:
   Said hollow plunging tube set to an open position creates a seal cavity within said perforated plunging seal.

7. The syringe device of claim 6 wherein:
   Said hollow plunging tube is rotated in an opening direction to said open position such that said at least one seal hole in said perforated plunger seal and said at least one tube hole on said sealed bottom of said plunging tube permits liquids to flow from the hollow syringe barrel cavity of said hollow syringe barrel, through the seal cavity, and into a hollow plunging tube cavity of said hollow plunging tube.

8. The syringe device of claim 6 wherein:
   Said hollow plunging tube is rotated in a closing direction to a closed position such that said at least one seal hole and at least one tube hole are misaligned to prevent liquids from moving from the hollow syringe barrel cavity of said hollow syringe barrel into a hollow plunging tube cavity of said hollow plunging tube.

* * * * *